US009127279B2

(12) United States Patent
Calvez et al.

(10) Patent No.: US 9,127,279 B2
(45) Date of Patent: Sep. 8, 2015

(54) USE OF INTERFERING RNA FOR TREATING AN HIV INFECTION

(75) Inventors: Vincent Calvez, Paris (FR); Anne-Geneviève Marcelin, Paris (FR)

(73) Assignees: UNIVERSITE PIERRE ET MARIE CURIE (PARIS 6), Paris (FR); ASSISTANCE PUBLIQUE-HOPITAUX DE PARIS, Paris (FR)

( * ) Notice: Subject to any disclaimer, the term of this patent is extended or adjusted under 35 U.S.C. 154(b) by 190 days.

(21) Appl. No.: 13/378,754

(22) PCT Filed: Jun. 28, 2010

(86) PCT No.: PCT/FR2010/051328
§ 371 (c)(1),
(2), (4) Date: Dec. 16, 2011

(87) PCT Pub. No.: WO2011/001086
PCT Pub. Date: Jan. 6, 2011

(65) Prior Publication Data
US 2012/0095082 A1      Apr. 19, 2012

(30) Foreign Application Priority Data
Jun. 29, 2009   (FR) ..................................... 09 54418

(51) Int. Cl.
*C12N 15/113*   (2010.01)
*C07K 14/005*   (2006.01)

(52) U.S. Cl.
CPC .......... *C12N 15/1137* (2013.01); *C07K 14/005* (2013.01); *C12N 15/1132* (2013.01); *C12Y 207/07049* (2013.01); *C12N 2310/14* (2013.01); *C12N 2310/141* (2013.01); *C12N 2320/31* (2013.01); *C12N 2740/16222* (2013.01)

(58) Field of Classification Search
USPC ................. 435/6, 91.1, 91.31, 455, 5, 235.1; 514/1, 2, 44; 536/23.1, 24.5, 24.32; 506/9, 16
See application file for complete search history.

(56) References Cited

U.S. PATENT DOCUMENTS

| 2007/0087335 | A1* | 4/2007 | Brahmachari et al. | ............. 435/5 |
| 2009/0004668 | A1* | 1/2009 | Chen et al. | ......................... 435/6 |
| 2009/0010908 | A1* | 1/2009 | Gow et al. | ..................... 424/94.1 |
| 2010/0173288 | A1* | 7/2010 | Zhang et al. | ....................... 435/6 |
| 2010/0173795 | A1* | 7/2010 | Kozal | ................................. 506/9 |
| 2012/0094896 | A1* | 4/2012 | Sandrock et al. | ............... 514/3.8 |
| 2013/0059865 | A1* | 3/2013 | Deadman et al. | ......... 514/259.41 |

FOREIGN PATENT DOCUMENTS

WO    WO 2007/042899         4/2007

OTHER PUBLICATIONS

Doench et al., Genes and Development, vol. 18, No. 5, pp. 504-511 (2004).*
Opalinska et al., Nature Rev., vol. 1, pp. 503-514 (2002).*
Nitshitsuji et al., J. Virology, vol. 80, No. 15, pp. 7658-7666 (2006).*
Shafer et al., AIDS Rev., vol. 10, pp. 67-84 (2008).*
Doench et al, Genes & Development, vol. 18, pp. 504-511 (2004).*
Nishitsuji, H. et al. "Effective Suppression of Human Immunodeficiency Virus Type 1 through a Combination of Short- or Long-Harpin RNAs Targeting Essential Sequences for Retroviral Integration" *Journal of Virology*, Aug. 2006, pp. 7658-7666, vol. 80, No. 15.
Shafer, R. W. et al. "HIV-1 Drug Resistance Mutations: an Updated Framework for the Second Decade of HAART" *AIDS Reviews*, Apr. 2, 2008, pp. 67-84, vol. 10, No. 2.
Johnson, V. A. et al. "Update of the Drug Resistance Mutations in HIV-1: Dec. 2008" *Topics in HIV Medicine*, Dec. 2008, pp. 138-145, vol. 16, No. 5.
Von Eije, K. J. et al. "Human Immunodeficiency Virus Type 1 Escape Is Restricted When Conserved Genome Sequences Are Targeted by RNA Interference" *Journal of Virology*, Mar. 2008, pp. 2895-2903, vol. 82, No. 6.
Huelsmann, P. M. et al. "Inhibition of drug-resistant HIV-1 by RNA interference" *Antiviral Research*, Jan. 1, 2006, pp. 1-8, vol. 69, No. 1.
Written Opinion in International Application No. PCT/FR2010/051328, Dec. 29, 2010, pp. 1-9.

* cited by examiner

*Primary Examiner* — Jane Zara
(74) *Attorney, Agent, or Firm* — Saliwanchik, Lloyd & Eisenschenk

(57) ABSTRACT

The present invention relates to interfering RNAs, in particular miRNAs, capable of specifically blocking the replication of a strain of the HIV virus that is resistant to an antiretroviral compound, and use thereof for treating infections by this type of virus.

16 Claims, No Drawings

SEQUENCE LISTING

<160> NUMBER OF SEQ ID NOS: 16

<210> SEQ ID NO 1
<211> LENGTH: 288
<212> TYPE: PRT
<213> ORGANISM: Human immunodeficiency virus type 1

<400> SEQUENCE: 1

Phe Leu Asp Gly Ile Asp Lys Ala Gln Glu Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
             35                  40                  45

Ala Met His Gly Gln Val Asp Cys Ser Pro Gly Ile Trp Gln Leu Asp
 50                  55                  60

Cys Thr His Leu Glu Gly Lys Val Ile Leu Val Ala Val His Val Ala
 65                  70                  75                  80

Ser Gly Tyr Ile Glu Ala Glu Val Ile Pro Ala Glu Thr Gly Gln Glu
                 85                  90                  95

Thr Ala Tyr Phe Leu Leu Lys Leu Ala Gly Arg Trp Pro Val Lys Thr
                100                 105                 110

Val His Thr Asp Asn Gly Ser Asn Phe Thr Ser Thr Thr Val Lys Ala
            115                 120                 125

Ala Cys Trp Trp Ala Gly Ile Lys Gln Glu Phe Gly Ile Pro Tyr Asn
            130                 135                 140

Pro Gln Ser Gln Gly Val Ile Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asp Pro Val Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
            275                 280                 285

<210> SEQ ID NO 2
<211> LENGTH: 23
<212> TYPE: RNA
<213> ORGANISM: Homo sapiens

<400> SEQUENCE: 2
acugcccuaa gugcuccuuc ugg                                           23

<210> SEQ ID NO 3
<211> LENGTH: 22
<212> TYPE: RNA
<213> ORGANISM: Homo sapiens

<400> SEQUENCE: 3
uauugcacuu gucccggccu gu                                            22

<210> SEQ ID NO 4
<211> LENGTH: 22
<212> TYPE: RNA
<213> ORGANISM: Homo sapiens

<400> SEQUENCE: 4
aggggcuggc uuuccucugg uc                                            22

```
<210> SEQ ID NO 5
<211> LENGTH: 22
<212> TYPE: RNA
<213> ORGANISM: Homo sapiens

<400> SEQUENCE: 5
agaguugagu cuggacgucc cg                                              22

<210> SEQ ID NO 6
<211> LENGTH: 22
<212> TYPE: RNA
<213> ORGANISM: Homo sapiens

<400> SEQUENCE: 6
gccugcuggg guggaaccug gu                                              22

<210> SEQ ID NO 7
<211> LENGTH: 23
<212> TYPE: RNA
<213> ORGANISM: Homo sapiens

<400> SEQUENCE: 7
ucucuggagg gaagcacuuu cug                                             23

<210> SEQ ID NO 8
<211> LENGTH: 21
<212> TYPE: RNA
<213> ORGANISM: Homo sapiens

<400> SEQUENCE: 8
gaagugugcc gugguguguc u                                               21

<210> SEQ ID NO 9
<211> LENGTH: 20
<212> TYPE: RNA
<213> ORGANISM: Homo sapiens

<400> SEQUENCE: 9
aggaauguuc cuucuuugcc                                                 20

<210> SEQ ID NO 10
<211> LENGTH: 24
<212> TYPE: RNA
<213> ORGANISM: Homo sapiens

<400> SEQUENCE: 10 ugggagcug aggcucuggg ggug                                             24

<210> SEQ ID NO 11
<211> LENGTH: 21
<212> TYPE: RNA
<213> ORGANISM: Homo sapiens

<400> SEQUENCE: 11
gugggcgggg gcaggugugu g                                               21

<210> SEQ ID NO 12
<211> LENGTH: 20
<212> TYPE: RNA
<213> ORGANISM: Homo sapiens

<400> SEQUENCE: 12
gugucugggc ggacagcugc                                                 20
```

-continued

<210> SEQ ID NO 13
<211> LENGTH: 22
<212> TYPE: RNA
<213> ORGANISM: Homo sapiens

<400> SEQUENCE: 13
cgcaggggcc gggugcucac cg                                              22

<210> SEQ ID NO 14
<211> LENGTH: 578
<212> TYPE: PRT
<213> ORGANISM: Human immunodeficiency virus type 1

<400> SEQUENCE: 14

Pro Ile Ser Pro Ile Asp Thr Val Pro Val Thr Leu Lys Pro Gly Met
1               5                   10                  15

Asp Gly Pro Lys Val Lys Gln Trp Pro Leu Thr Glu Glu Lys Ile Lys
            20                  25                  30

Ala Leu Thr Glu Ile Cys Lys Glu Met Glu Lys Glu Gly Lys Ile Ser
        35                  40                  45

Lys Ile Gly Pro Glu Asn Pro Tyr Asn Thr Pro Val Phe Ala Ile Lys
    50                  55                  60

Lys Lys Asp Ser Thr Lys Trp Arg Lys Leu Val Asp Phe Arg Glu Leu
65                  70                  75                  80

Asn Lys Arg Thr Gln Asp Phe Trp Glu Val Gln Leu Gly Ile Pro His
                85                  90                  95

Pro Ala Gly Leu Lys Lys Lys Lys Ser Val Thr Val Leu Asp Val Gly
            100                 105                 110

Asp Ala Tyr Phe Ser Val Pro Leu Asp Glu Ser Phe Arg Lys Tyr Thr
        115                 120                 125

Ala Phe Thr Ile Pro Ser Met Asn Asn Glu Thr Pro Gly Ile Arg Tyr
    130                 135                 140

Gln Tyr Asn Val Leu Pro Gln Gly Trp Lys Gly Ser Pro Ala Ile Phe
145                 150                 155                 160

Gln Ser Ser Met Thr Lys Ile Leu Glu Pro Phe Arg Ile Lys Asn Pro
                165                 170                 175

Glu Met Val Ile Tyr Gln Tyr Met Asp Asp Leu Tyr Val Gly Ser Asp
            180                 185                 190

Leu Glu Ile Gly Gln His Arg Thr Lys Ile Glu Glu Leu Arg Ala His
        195                 200                 205

Leu Leu Arg Trp Gly Phe Thr Thr Pro Asp Lys Lys His Gln Lys Glu
    210                 215                 220

Pro Pro Phe Leu Trp Met Gly Tyr Glu Leu His Pro Asp Arg Trp Thr
225                 230                 235                 240

Val Gln Pro Ile Glu Leu Pro Glu Lys Asp Ser Trp Thr Val Asn Asp
                245                 250                 255

Ile Gln Lys Leu Val Gly Lys Leu Asn Trp Ala Ser Gln Ile Tyr Ala
            260                 265                 270

Gly Ile Lys Val Lys Gln Leu Cys Lys Leu Leu Arg Gly Ala Lys Ala
        275                 280                 285

Leu Thr Glu Val Val Pro Leu Thr Glu Glu Ala Glu Leu Glu Leu Ala
    290                 295                 300

Glu Asn Arg Glu Ile Leu Lys Thr Pro Val His Gly Val Tyr Tyr Asp
305                 310                 315                 320

Pro Ser Lys Asp Leu Val Val Glu Val Gln Lys Gln Gly Gln Asp Gln
                325                 330                 335

-continued

```
Trp Thr Tyr Gln Ile Tyr Gln Glu Pro Phe Lys Asn Leu Lys Thr Gly
            340                 345                 350
Lys Tyr Ala Arg Lys Arg Ser Ala His Thr Asn Asp Val Arg Gln Leu
        355                 360                 365
Ala Glu Val Val Gln Lys Val Ala Thr Glu Ser Ile Val Ile Trp Gly
    370                 375                 380
Lys Ile Pro Lys Phe Arg Leu Pro Ile Gln Arg Glu Thr Trp Glu Thr
385                 390                 395                 400
Trp Trp Met Glu Tyr Trp Gln Ala Thr Trp Ile Pro Glu Trp Glu Phe
                405                 410                 415
Val Asn Thr Pro Pro Leu Val Lys Leu Trp Tyr Gln Leu Glu Lys Asp
            420                 425                 430
Pro Ile Val Gly Ala Glu Thr Phe Tyr Val Asp Gly Ala Ala Ser Arg
        435                 440                 445
Glu Thr Lys Leu Gly Lys Ala Gly Tyr Val Thr Asn Arg Gly Arg Gln
    450                 455                 460
Lys Val Val Ser Leu Thr Glu Thr Thr Asn Gln Lys Thr Glu Leu His
465                 470                 475                 480
Ala Ile His Leu Ala Leu Gln Asp Ser Gly Ser Glu Val Asn Ile Val
                485                 490                 495
Thr Asp Ser Gln Tyr Ala Leu Gly Ile Ile Gln Ala Gln Pro Asp Arg
            500                 505                 510
Ser Glu Ser Glu Val Val Asn Gln Ile Ile Glu Gln Leu Ile Lys Lys
        515                 520                 525
Glu Lys Val Tyr Leu Ser Trp Val Pro Ala His Lys Gly Ile Gly Gly
    530                 535                 540
Asn Glu Gln Val Asp Lys Leu Val Ser Ser Gly Ile Arg Lys Val Leu
545                 550                 555                 560
Phe Leu Asp Gly Ile Asp Lys Ala Gln Glu Glu His Glu Arg Tyr His
                565                 570                 575
Ser Asn

<210> SEQ ID NO 15
<211> LENGTH: 23
<212> TYPE: RNA
<213> ORGANISM: Homo sapiens

<400> SEQUENCE: 15
agcugguguu gugaaucagg ccg                                          23

<210> SEQ ID NO 16
<211> LENGTH: 20
<212> TYPE: RNA
<213> ORGANISM: Homo sapiens

<400> SEQUENCE: 16
aggguguuuc ucucaucucu                                              20
```

USE OF INTERFERING RNA FOR TREATING AN HIV INFECTION

CROSS-REFERENCE TO RELATED APPLICATION

This application is the U.S. national stage application of International Patent Application No. PCT/FR2010/051328, filed Jun. 28, 2010.

The present invention relates to the field of medicine, and more particularly to the field of the treatment of HIV virus infections. It notably relates to interfering RNAs capable of specifically blocking the replication of a strain of the HIV virus that is resistant to an antiretroviral compound and use thereof for treating infections by this type of virus.

TECHNOLOGICAL BACKGROUND OF THE INVENTION

The human immunodeficiency virus, or HIV, is a retrovirus of the lentivirus genus which infects humans and is responsible for the acquired immunodeficiency syndrome (AIDS). Although there are antiretroviral treatments for delaying the appearance of AIDS, no vaccine or definitive treatment is available at present.

HIV has an envelope composed in part of the membrane of the infected cell from which it has come and two types of glycoproteins, namely gp120 and gp41. Inside the envelope there is a protein matrix composed of p17 proteins and containing the capsid consisting of p24 proteins and the nucleocapsid consisting of p6 and p7 proteins. The genome of HIV is a single-stranded RNA which is contained in the capsid in the presence of two enzymes, reverse transcriptase p64 required for transcription of the viral RNA into DNA, and integrase p32 required for integration of the viral DNA into the DNA of the infected cell. These two enzymes as well as protease p10, which participates in assembly of the viral particle, are specific to the retroviruses and are therefore the main targets of antiretroviral treatments.

In the last five years, the arsenal of the antiretrovirals has been enriched with nine new molecules and with three new classes of inhibitors. The purpose of the antiretrovirals is to interfere with various mechanisms: on the one hand, the enzymes of HIV required for its replication and on the other hand, the mechanisms by which it enters the cell. The target proteins of these molecules are therefore essentially reverse transcriptase, integrase, protease and the glycoprotein gp41. Among the most recent antiretrovirals, raltegravir, the first representative of the class of integrase inhibitors (INIs), has recently obtained Marketing Authorization. Elvitegravir, the second product of this class, is currently undergoing clinical trials. The results of the various clinical studies that evaluated the use of these two molecules are very encouraging with regard to virological success, tolerance and immunological response. However, as with other antiretrovirals, resistances to INI appear in studies in vitro and in vivo. These resistances are characterized by the selection of mutations on the gene of the integrase of HIV which have an impact on the sensitivity of the virus to the INIs. The mutations found in patients for whom the therapy failed are mainly localized in the central catalytic domain of the enzyme located between amino acids 50 and 212.

The phenomenon of resistance of HIV to antiretrovirals is a major problem in antiretroviral therapy as it leads to a decrease in efficacy of the treatments and an increase in patient mortality.

Earlier work demonstrated the interaction between microRNAs (miRNAs) and viruses. The miRNAs are single-stranded RNAs with a length of about 21 to 24 nucleotides. There are several hundred microRNA genes in the genomes of most multicellular organisms and, to date, about 500 miRNAs have been identified in humans. The miRNAs are post-transcriptional repressors: by pairing with messenger RNAs, they guide their degradation, or repression of their translation into protein. The miRNA genes are transcribed in the form of long precursors called "pri-miRNA". These precursors are cleaved in the nucleus to an intermediate called "pre-miRNA" by a complex called Microprocessor which is formed in animals by the enzymes Drosha and DGCR8 (Di George Critical Region 8 or Pasha) and in plants by an enzyme of the Dicer family. Pre-miRNA is an RNA with a length of about 70 nucleotides, folded into an imperfect stem-and-loop by base complementarity between the first half and the second half of its sequence. This pre-miRNA is transported from the nucleus to the cytosol by GTP-dependent active transport through interaction with exportin 5. The pre-miRNA is then cleaved in the cytoplasm by an enzyme of the Dicer family to release a small double-stranded RNA called "miRNA". This double-stranded miRNA then interacts with a protein of the Argonaute family (Ago1 or Ago2) to form the RISC complex (RNA-induced Silencing Complex). This complex of about 160 kDa has been described as being sufficient for the activity of the miRNAs of repression of translation. However, other proteins such as geminin can also be added to the complex. During formation of the RISC complex, the double-stranded miRNA becomes single-stranded and only the strand specific to the target mRNA is conserved. The target mRNA is then loaded within the RISC complex. At this stage, two routes are then possible depending on the composition of the complex. In the case when the complex contains the protein Ago2, the target mRNA will be degraded. If the complex contains the protein Ago1, translation of the target mRNA will be then repressed.

It has already been demonstrated that certain miRNAs of the host cells are capable of targeting viral RNAs and therefore possess an antiviral role or conversely allow the virus to accumulate in the cell. This situation has notably been described for the miRNA hsa-miR-122a specifically expressed in the liver and promoting replication of the RNA of the hepatitis B virus (Chen et al., 2007).

SUMMARY OF THE INVENTION

The aim of the present invention is to provide novel compounds that can be used in the treatment of an infection by a strain of the HIV virus that is resistant to an antiretroviral compound.

The inventors have demonstrated the existence of miRNAs capable of hybridizing preferentially to the genes of strains of HIV that are resistant to antiretrovirals, notably to inhibitors of integrase or of reverse transcriptase. The studies presented in this document show that these miRNAs possess antiviral activity and are notably able to block the replication and viral production of HIV.

Thus, the present invention relates to an interfering RNA that hybridizes preferentially to the mRNA of a gene coding for a mutant protein of a strain of the HIV virus, said mutant protein containing one or more mutations endowing the viral strain with a phenotype of resistance to an antiretroviral compound, for use in the treatment of an infection by a strain of the HIV virus resistant to said antiretroviral compound. Preferably, the HIV virus is the HIV-1 virus.

According to one embodiment, the interfering RNA is selected from the group consisting of an siRNA, an shRNA and an miRNA. Preferably, the interfering RNA is an miRNA.

According to one embodiment, the mutant protein is selected from the group consisting of reverse transcriptase, protease, glycoprotein gp41 and integrase.

According to a particular embodiment, the mutant protein is the integrase of the HIV-1 virus and the antiretroviral compound is an integrase inhibitor, preferably raltegravir or elvitegravir. According to one embodiment, the integrase contains one or more mutations endowing the viral strain with a phenotype of resistance to said integrase inhibitor, the mutated residue or residues of integrase being selected from the group consisting of the residue T66, E92, F121, E138, G140, Y143, S147, Q148, S153, N155, E157 and R263 of SEQ ID No. 1, and a combination thereof. Preferably, the mutation or mutations are selected from the group consisting of E92Q, G140S, G140A and Y143R, and a combination thereof.

According to a particular embodiment, the interfering RNA is an miRNA selected from the group consisting of hsa-miR-18a (SEQ ID No:2), hsa-miR-92a-1 (SEQ ID No:3), hsa-miR-185* (SEQ ID No:4), hsa-miR-219-1-3p (SEQ ID No:5), hsa-miR-370 (SEQ ID No:6), hsa-miR-518c* (SEQ ID No:7), hsa-miR-595 (SEQ ID No:8), hsa-miR-613 (SEQ ID No:9), hsa-miR-939 (SEQ ID No:10), hsa-miR-1228* (SEQ ID No:11), hsa-miR-1231 (SEQ ID No:12) and hsa-miR-1909 (SEQ ID No:13), and a combination thereof.

According to another embodiment, the mutant protein is the reverse transcriptase of the HIV-1 virus and the antiretroviral compound is an inhibitor of reverse transcriptase. Preferably, the reverse transcriptase contains one or more mutations endowing the viral strain with a phenotype of resistance to said inhibitor of reverse transcriptase, the mutated residue or residues of reverse transcriptase being selected from the group consisting of residue D67 and T215 of SEQ ID No. 14, and a combination thereof. According to a particular embodiment, the interfering RNA is an miRNA selected from the group consisting of hsa-miR-138 (SEQ ID No:15) and hsa-miR-609 (SEQ ID No:16), and a combination thereof.

In a second aspect, the present invention relates to an expression vector comprising a nucleotide sequence coding for one of the interfering RNAs used according to the invention or coding for a precursor thereof, for use in the treatment of an infection by a strain of the HIV virus that is resistant to an antiretroviral compound.

In another aspect, the present invention also relates to an interfering RNA that hybridizes preferentially to the mRNA of a gene coding for a mutant protein of a strain of the HIV virus, said mutant protein containing one or more mutations endowing the viral strain with a phenotype of resistance to an antiretroviral compound, or an expression vector comprising a nucleotide sequence coding for said interfering RNA or for a precursor thereof, for use in combination with said antiretroviral compound in the treatment of an infection by the HIV virus. Preferably, the antiretroviral compound is an inhibitor of integrase or of reverse transcriptase.

In yet another aspect, the present invention relates to a pharmaceutical composition comprising at least one interfering RNA according to the invention and/or an expression vector according to the invention, and one or more pharmaceutically acceptable excipients and/or vehicles. Preferably, the pharmaceutical composition comprises at least one miRNA selected from the group consisting of hsa-miR-185* (SEQ ID No:4), hsa-miR-370 (SEQ ID No:6), hsa-miR-518c* (SEQ ID No:7), hsa-miR-595 (SEQ ID No:8), hsa-miR-609 (SEQ ID No:16), hsa-miR-613 (SEQ ID No:9), hsa-miR-939 (SEQ ID No:10), hsa-miR-1228* (SEQ ID No:11), hsa-miR-1231 (SEQ ID No:12) and hsa-miR-1909 (SEQ ID No:13), and a combination thereof. According to one embodiment, the pharmaceutical composition further comprises one or more antiretroviral compounds.

DETAILED DESCRIPTION OF THE INVENTION

The inventors identified sequences of miRNA that are able to attach specifically to the nucleotide sequences of strains of HIV bearing mutations of resistance to an antiretroviral compound. They also demonstrated that these miRNAs were thus capable of particularly effectively blocking the viral replication of said resistant strains.

Thus, in a first aspect, the present invention relates to an interfering RNA that hybridizes preferentially to the mRNA of a gene coding for a mutant protein of a strain of the HIV virus, said mutant protein containing one or more mutations endowing the viral strain with a phenotype of resistance to an antiretroviral compound, for use in the treatment of an infection by a strain of the HIV virus resistant to said antiretroviral compound.

RNA interference is a phenomenon that is well known to a person skilled in the art, permitting specific inhibition of expression of the target gene at the post-transcriptional level. The term "interfering RNA" or "RNAi", as used in the present document, refers to any RNA, single or double stranded, that interferes with a specific messenger RNA thus leading to its degradation and/or to a decrease in its translation into protein. This term includes small interfering RNAs (siRNAs), double-stranded RNAs (dsRNAs), single-stranded RNAs (ssRNAs), short hairpin RNAs (shRNAs), DNA-directed RNAi (ddRNAi) and microRNAs (miRNAs).

The interfering RNAs used according to the invention can be of the single-stranded or double-stranded form or a mixture of the two. They can contain modified nucleotides or chemical modifications enabling them, for example, to increase their resistance to nucleases and thus increase their lifetime in the cell. They can notably comprise at least one modified or non-natural nucleotide such as, for example, a nucleotide having a modified base, such as inosine, methyl-5-deoxycytidine, dimethylamino-5-deoxyuridine, deoxyuridine, diamino-2,6-purine, bromo-5-deoxyuridine or any other modified base permitting hybridization. The interfering RNAs used according to the invention can also be modified at the internucleotide bond, for example phosphorothioates, H-phosphonates or alkyl phosphonates, or in the backbone, for example alpha-oligonucleotides, 2'-O-alkyl ribose or PNAs (peptide nucleic acids) (M. Egholm et al., 1992).

The interfering RNAs can be natural RNAs, synthetic RNAs or those produced by recombination techniques. These interfering RNAs can be prepared by any methods known to a person skilled in the art, such as, for example, chemical synthesis, screening of databases, transcription in vivo or recombinant DNA or amplification techniques.

According to one embodiment, the interfering RNA is selected from the group consisting of an siRNA, an shRNA and an miRNA.

According to a particular embodiment, the interfering RNA is an siRNA of double-stranded form with a length of about 15 to 50 nucleotides, preferably about 15 to 30 nucleotides. The siRNAs are perfectly complementary to their target mRNAs.

According to another particular embodiment, the interfering RNA is an shRNA of single-stranded form, in stem-and-loop form, of about 25 to 30 nucleotides and in which the size of the loop is from 4 to 23 nucleotides.

According to a preferred embodiment, the interfering RNA is an miRNA. The term "miRNA" or "microRNA" encompasses single-stranded and double-stranded miRNAs. Preferably, the miRNAs are of double-stranded form. The miRNAs are partially complementary to their target mRNAs and have a size between 10 and 25 nucleotides, preferably between 20 and 25 nucleotides. The miRNAs used according to the invention can be administered in the form of precursors. The miRNAs can notably be administered in the form of pre-miRNAs or of pri-miRNAs. The pri-miRNAs are precursors of miRNA which are cleaved in the nucleus of the cells to form pre-miRNAs. A pri-miRNA can comprise one or more pre-miRNAs. The pre-miRNAs are also precursors of the miRNAs. They comprise between 60 and 80 nucleotides and are folded into an imperfect stem-and-loop structure. These pre-miRNAs are cleaved in the cytoplasm to form double-stranded miRNAs and then single-stranded miRNAs capable of interacting with a protein of the Argonaute family to form the RISC complex, owing to which either the target mRNA is degraded, or the translation of this mRNA is repressed.

The term "which hybridizes" signifies, in the present document, that hydrogen bonds of the Watson-Crick type can be established between the complementary bases of two strands of nucleic acid to form a duplex. The term "which hybridizes preferentially" signifies in the present document that the interfering RNA used according to the invention is capable of hybridizing to a gene or a transcript coding for a mutant protein of a strain of the HIV virus in conditions of hybridization of high or medium stringency. The conditions of high or medium stringency are described extensively in the literature, for example in Sambrook et al., (1989), Maniatis et al., (1982 or one of its later editions) and in Ausubel et al., (1995), and these conditions can be adapted by a person skilled in the art in relation to the size of the nucleotide fragments, according to appropriate known teachings.

The capacity of the interfering RNA used according to the invention to hybridize preferentially to a gene or a transcript coding for a mutant protein of a strain of the HIV virus can also be evaluated by means of a competitive assay. The interfering RNA is put in the presence of an equivalent amount (i) of the gene or of the transcript of a protein of an HIV strain that is not resistant to an antiretroviral compound and (ii) of the gene or of the transcript of the same protein derived from an HIV strain resistant to an antiretroviral compound and bearing one or more mutations. This mixing is performed in conditions of medium or high stringency permitting hybridization. The interfering RNA hybridizes preferentially to a gene or a transcript coding for a mutant protein of a strain of the HIV virus if, in these conditions, at least 60% of the interfering RNA hybridizes to the gene or the transcript of the mutant protein, preferably at least 70%, and quite particularly preferably at least 80%, at least 90% or at least 95%, and if less than 40% of the interfering RNA hybridizes to the gene or the transcript of the non-mutated protein, preferably less than 20%, less than 15%, less than 10% or less than 5%.

The capacity of the interfering RNA used according to the invention to hybridize preferentially to a gene or a transcript coding for a mutant protein of a strain of the HIV virus can also be evaluated by means of bioinformatic tools well known to a person skilled in the art.

In the context of the present invention, the term "mRNA of a gene coding for a protein" is employed to denote the ribonucleotide sequence derived from transcription of the gene coding for the corresponding protein. This term includes the untranslated regions at 3' and at 5' (3'-UTR and 5'-UTR), exons and, optionally, unspliced introns.

The HIV virus can be of the HIV-1 or HIV-2 type, preferably of the HIV-1 type.

As used in the present document, the term "strain of HIV virus resistant to an antiretroviral compound" denotes a strain of HIV for which the administration of said antiretroviral compound has no effect, or has a reduced effect, on viral replication or production.

The mutant protein endowing the viral strain with a phenotype of resistance to an antiretroviral compound can be any protein encoded by the genome of the HIV virus such as, for example, reverse transcriptase, protease, glycoprotein gp41, integrase, protein p17, protein p24, protein p7, protein p6 or glycoprotein gp120. Preferably, the mutant protein is selected from the group consisting of reverse transcriptase, protease, glycoprotein gp41 and integrase.

The term "antiretroviral compound" as used in this document denotes a molecule used for treating infections linked to retroviruses, notably to HIV. These molecules are essentially directed against enzymes or other molecules specific to this type of virus. The antiretroviral molecules can be inhibitors of reverse transcriptase, i.e. nucleoside inhibitors such as zidovudine, lamivudine, emtricitabine, didanosine, stavudine, abacavir, zalcitabine or tenofovir, non-nucleoside inhibitors such as efavirenz, nevirapine, etravirine or delavirdine, or nucleotide analogues such as tenofovir or fosalvudine; protease inhibitors such as amprenavir, tipranavir, indinavir, saquinavir, fosamprenavir, ritonavir, darunavir, atazanavir or nelfinavir; fusion inhibitors such as enfuvirtide; entry inhibitors such as maraviroc, vicriviroc or TNX-355; maturation inhibitors such as bevirimat; or integrase inhibitors such as raltegravir, elvitegravir or MK-2048.

According to a particular embodiment, the mutant protein is integrase and the antiretroviral compound is an integrase inhibitor. In the case of a virus that is not resistant to integrase inhibitors, the latter block the action of integrase and thus prevent the viral genome binding to that of the target cell. According to this embodiment of the invention, the integrase contains one or more mutations endowing the viral strain with a phenotype of resistance to an integrase inhibitor, preferably raltegravir (Isentress or MK-0518, CAS number 518048-05-0) or elvitegravir (JTK-303 or GS 9137, CAS number 697761-98-1). In particular, the mutated residue or residues are selected from the group consisting of the residue T66, E92, F121, E138, G140, Y143, S147, Q148, S153, N155, E157 and R263 of SEQ ID No. 1, and a combination thereof. Preferably, the mutated residue or residues are selected from the group consisting of residue E92, G140 and Y143 of SEQ ID No. 1, and a combination thereof. Quite particularly preferably, the mutation or mutations are selected from the group consisting of E92Q, G140S, G140A, Y143R and Y143C, and a combination thereof.

The amino acid residues are identified in the present document by the single-letter code of the amino acid and its position in the protein sequence. The universally recognized single-letter code of the amino acids is as follows: G for Glycine, P for Proline, A for Alanine, V for Valine, L for Leucine, I for Isoleucine, M for Methionine, C for Cysteine, F for Phenylalanine, Y for Tyrosine, W for Tryptophan, H for Histidine, K for Lysine, R for Arginine, Q for Glutamine, N for Asparagine, E for glutamic acid, D for aspartic acid, S for Serine and T for Threonine. As an example, the residue T66 therefore corresponds to a threonine in position 66 of the protein sequence.

The mutations of amino acids are identified in the present document by the single-letter code of the mutated amino acid followed by its position in the protein sequence and of the single-letter code of the amino acid replacing the initial amino acid. As an example, the mutation E92Q corresponds to substitution of the glutamic acid in position 92 with a glutamine.

According to a preferred embodiment, the mutant protein is integrase, the antiretroviral compound is an integrase inhibitor and the interfering RNA used according to the invention is an miRNA selected from the group consisting of hsa-miR-18a (SEQ ID No:2), hsa-miR-92a-1 (SEQ ID No:3), hsa-miR-185* (SEQ ID No:4), hsa-miR-219-1-3p (SEQ ID No:5), hsa-miR-370 (SEQ ID No:6), hsa-miR-518c* (SEQ ID No:7), hsa-miR-595 (SEQ ID No:8), hsa-miR-613 (SEQ ID No:9), hsa-miR-939 (SEQ ID No:10), hsa-miR-1228* (SEQ ID No:11), hsa-miR-1231 (SEQ ID No:12) and hsa-miR-1909 (SEQ ID No:13), and a combination thereof. In particular, the miRNA is selected from the group consisting of hsa-miR-185* (SEQ ID No:4), hsa-miR-370 (SEQ ID No:6), hsa-miR-518c* (SEQ ID No:7), hsa-miR-595 (SEQ ID No:8), hsa-miR-939 (SEQ ID No:10), hsa-miR-1228* (SEQ ID No:11), hsa-miR-1231 (SEQ ID No:12) and hsa-miR-1909 (SEQ ID No:13), and a combination thereof. Preferably, the miRNA is selected from the group consisting of hsa-miR-518c* (SEQ ID No:7), hsa-miR-939 (SEQ ID No:10), hsa-miR-1231 (SEQ ID No:12) and hsa-miR-1909 (SEQ ID No:13), and a combination thereof.

According to a particular embodiment, the integrase comprises the mutation E92Q in SEQ ID No. 1 and the interfering RNA used according to the invention is an miRNA selected from the group consisting of hsa-miR-1231 (SEQ ID No:12), hsa-miR-370 (SEQ ID No:6) and hsa-miR-18a (SEQ ID No:2), and a combination thereof. According to another particular embodiment, the integrase comprises the mutation G140S in SEQ ID No. 1 and the interfering RNA used according to the invention is an miRNA selected from the group consisting of hsa-miR-939 (SEQ ID No:10) and hsa-miR-185* (SEQ ID No:4), and a combination thereof. According to yet another particular embodiment, the integrase comprises the mutation G140A in SEQ ID No. 1 and the interfering RNA used according to the invention is an miRNA selected from the group consisting of hsa-miR-92a-1 (SEQ ID No:3) and hsa-miR-219-1-3p (SEQ ID No:5), and a combination thereof. According to yet another particular embodiment, the integrase comprises the mutation Y143C in SEQ ID No. 1 and the interfering RNA used according to the invention is the miRNA hsa-miR-1909 (SEQ ID No:13). According to yet another particular embodiment, the integrase comprises the mutation Y143R in SEQ ID No. 1 and the interfering RNA used according to the invention is an miRNA selected from the group consisting of hsa-miR-613 (SEQ ID No:9) and hsa-miR-1228* (SEQ ID No:11), and a combination thereof.

According to another particular embodiment, the mutant protein is reverse transcriptase and the antiretroviral compound is an inhibitor of reverse transcriptase. In the case of a virus that is not resistant to inhibitors of reverse transcriptase, the latter block the synthesis of proviral DNA from the viral RNA. According to this embodiment of the invention, the reverse transcriptase contains one or more mutations endowing the viral strain with a phenotype of resistance to an inhibitor of reverse transcriptase. In particular, the mutated residue or residues are selected from the group consisting of residue D67 and T215 of SEQ ID No. 14, and a combination thereof.

According to a preferred embodiment, the mutant protein is reverse transcriptase, the antiretroviral compound is an inhibitor of reverse transcriptase and the interfering RNA used according to the invention is an miRNA selected from the group consisting of hsa-miR-138 (SEQ ID No:15) and hsa-miR-609 (SEQ ID No:16), and a combination thereof.

The interfering RNAs used according to the invention are capable of blocking or decreasing the viral replication and/or production of a strain of the HIV virus that is resistant to an antiretroviral compound. "Decrease" means a decrease of at least 30, 40, 50, 60, 70, 80 or 90% of the viral replication and/or of the viral production.

The interfering RNAs used according to the invention can be administered in the form of precursors or of DNA molecules coding for the latter.

In another aspect, the present invention relates to an expression vector comprising a nucleotide sequence coding for an interfering RNA that hybridizes preferentially to the mRNA of a gene coding for a mutant protein of a strain of the HIV virus, said mutant protein containing one or more mutations endowing the viral strain with a phenotype of resistance to an antiretroviral compound, or coding for a precursor thereof, for use in the treatment of an infection by a strain of the HIV virus that is resistant to an antiretroviral compound.

The expression vector according to the invention comprises the elements permitting expression of said nucleotide sequence in eukaryotic cells. Such vectors are well known to a person skilled in the art and were notably described in patent application WO 06/085016 or in the articles by Barton and Medzhitov, 2002; Tiscornia et al., 2004; Xia et al., 2002 and Shen et al., 2003.

The present invention also relates to an interfering RNA that hybridizes preferentially to the mRNA of a gene coding for a mutant protein of a strain of the HIV virus, said mutant protein containing one or more mutations endowing the viral strain with a phenotype of resistance to an antiretroviral compound, or an expression vector comprising a nucleotide sequence coding for said interfering RNA or a precursor of said RNA, for use in combination with said antiretroviral compound in the treatment of an infection by the HIV virus.

The interfering RNA or expression vector used according to the invention is as described above.

In particular, the antiretroviral compound is an integrase inhibitor or an inhibitor of reverse transcriptase.

According to a particular embodiment, the antiretroviral compound is an integrase inhibitor and the interfering RNA is an miRNA selected from the group consisting of hsa-miR-18a (SEQ ID No:2), hsa-miR-92a-1 (SEQ ID No:3), hsa-miR-185* (SEQ ID No:4), hsa-miR-219-1-3p (SEQ ID No:5), hsa-miR-370 (SEQ ID No:6), hsa-miR-518c* (SEQ ID No:7), hsa-miR-595 (SEQ ID No:8), hsa-miR-613 (SEQ ID No:9), hsa-miR-939 (SEQ ID No:10), hsa-miR-1228* (SEQ ID No:11), hsa-miR-1231 (SEQ ID No:12) and hsa-miR-1909 (SEQ ID No:13), and a combination thereof.

According to another particular embodiment, the antiretroviral compound is an inhibitor of reverse transcriptase and the interfering RNA is an miRNA selected from the group consisting of hsa-miR-138 (SEQ ID No:15) and hsa-miR-609 (SEQ ID No:16), and a combination thereof.

The interfering RNA used according to the invention and the antiretroviral compound can be administered simultaneously, if necessary within one and the same composition, or sequentially.

The present invention also relates to an interfering RNA that hybridizes preferentially to the mRNA of a gene coding for a mutant protein of a strain of the HIV virus, said mutant protein containing one or more mutations endowing the viral strain with a phenotype of resistance to an antiretroviral compound, or an expression vector comprising a nucleotide sequence coding for said interfering RNA or a precursor of said RNA, for the manufacture of a medicament for the treatment of an infection by a strain of the HIV virus resistant to said antiretroviral compound.

In another aspect, the present invention relates to a pharmaceutical composition comprising, as active substance, at least one interfering RNA which hybridizes preferentially to the mRNA of a gene coding for a mutant protein of a strain of the HIV virus, said mutant protein containing one or more mutations endowing the viral strain with a phenotype of resistance to an antiretroviral compound, and/or at least one expression vector comprising a nucleotide sequence coding for said interfering RNA or a precursor of said RNA, and one or more pharmaceutically acceptable excipients and/or vehicles.

The interfering RNA contained in the composition according to the invention can be any interfering RNA as described in the present application. Preferably, the interfering RNA is selected from the group consisting of an siRNA, an shRNA and an miRNA. Especially preferably, the interfering RNA is an miRNA.

According to one embodiment, the interfering RNA is an miRNA selected from the group consisting of hsa-miR-18a (SEQ ID No:2), hsa-miR-92a-1 (SEQ ID No:3), hsa-miR-185* (SEQ ID No:4), hsa-miR-219-1-3p (SEQ ID No:5), hsa-miR-370 (SEQ ID No:6), hsa-miR-518c* (SEQ ID No:7), hsa-miR-595 (SEQ ID No:8), hsa-miR-613 (SEQ ID No:9), hsa-miR-939 (SEQ ID No:10), hsa-miR-1228* (SEQ ID No:11), hsa-miR-1231 (SEQ ID No:12), hsa-miR-1909 (SEQ ID No:13), hsa-miR-138 (SEQ ID No:15) and hsa-miR-609 (SEQ ID No:16), and a combination thereof.

According to a particular embodiment, the interfering RNA is an miRNA selected from the group consisting of hsa-miR-185* (SEQ ID No:4), hsa-miR-370 (SEQ ID No:6), hsa-miR-518c* (SEQ ID No:7), hsa-miR-595 (SEQ ID No:8), hsa-miR-609 (SEQ ID No:16), hsa-miR-613 (SEQ ID No:9), hsa-miR-939 (SEQ ID No:10), hsa-miR-1228* (SEQ ID No:11), hsa-miR-1231 (SEQ ID No:12) and hsa-miR-1909 (SEQ ID No:13), and a combination thereof.

The composition according to the invention can also further comprise one or more antiretroviral compounds such as inhibitors of reverse transcriptase, protease inhibitors, fusion inhibitors, maturation inhibitors, or integrase inhibitors. In the case when the composition comprises several antiretroviral compounds, the latter can be inhibitors of the same type (inhibition of the same viral mechanism or of the same enzyme) or inhibitors of different types.

According to a particular embodiment, the composition according to the invention is a vaccine.

Advantageously, the vehicle of the present composition facilitates penetration of the interfering RNA or expression vector used according to the invention into the cells of the organism to be treated, and/or protects the interfering RNA or the expression vector against possible degradation that can adversely affect its efficacy. Among the vehicles that can be used, we may notably mention cationic polymers—natural such as chitosan or atelocollagen, or synthetic such as poly (L-lysine), polyethylenimine (PEI) or dendrimers, which form complexes with the nucleic acids of the invention; liposomes; cationic liposomes; galactosylated liposomes; liposomes covered with a ligand enabling them to target a type of cells such as immunoliposomes covered with an antibody specific to the target cell (Zheng et al., 2009); liposomes arranged within a nanoparticle formed by polymers (Carmona et al., 2009) or multilayer films of polycations and polyanions.

The composition according to the invention can be adapted for administration by the oral, sublingual, parenteral, topical, rectal or transdermal route according to the classical protocols that are well known to a person skilled in the art. Preferably, the composition is adapted for administration by the oral route, for example in the form of a tablet, a capsule, or an oral solution, or parenterally, in particular in the form of an injectable solution, notably by the intravenous, intradermal or subcutaneous route.

It is to be understood that the dose to be administered can be adjusted by a person skilled in the art in relation to many parameters such as the patient's physiology, the pathological state or the method of administration. Typically, the interfering RNAs are administered at doses that can vary between 0.1 and 20 mg per kilogram per day, preferably from 1 to 10 mg per kilogram per day. The administrations can be weekly or daily or even repeated several times a day. The interfering RNAs can be administered in the form of a unit dose comprising from 0.05 to 20 mg of interfering RNAs, preferably from 0.1 to 5 mg.

The present invention further relates to an interfering RNA according to the invention as a medicament. According to a particular embodiment, the interfering RNA is an miRNA selected from the group consisting of hsa-miR-18a (SEQ ID No:2), hsa-miR-92a-1 (SEQ ID No:3), hsa-miR-185* (SEQ ID No:4), hsa-miR-219-1-3p (SEQ ID No:5), hsa-miR-370 (SEQ ID No:6), hsa-miR-518c* (SEQ ID No:7), hsa-miR-595 (SEQ ID No:8), hsa-miR-613 (SEQ ID No:9), hsa-miR-939 (SEQ ID No:10), hsa-miR-1228* (SEQ ID No:11), hsa-miR-1231 (SEQ ID No:12), hsa-miR-1909 (SEQ ID No:13), hsa-miR-138 (SEQ ID No:15) and hsa-miR-609 (SEQ ID No:16), and a combination thereof. Preferably, the interfering RNA is an miRNA selected from the group consisting of hsa-miR-185* (SEQ ID No:4), hsa-miR-370 (SEQ ID No:6), hsa-miR-518c* (SEQ ID No:7), hsa-miR-595 (SEQ ID No:8), hsa-miR-609 (SEQ ID No:16), hsa-miR-613 (SEQ ID No:9), hsa-miR-939 (SEQ ID No:10), hsa-miR-1228* (SEQ ID No:11), hsa-miR-1231 (SEQ ID No:12) and hsa-miR-1909 (SEQ ID No:13), and a combination thereof.

The present invention also relates to a method of treatment of an infection by a strain of the HIV virus that is resistant to an antiretroviral compound comprising the administration to a subject, notably human, of a therapeutically effective amount of an interfering RNA, of an expression vector or of a pharmaceutical composition as defined above.

The term "treatment" as used in this document refers to an improvement or disappearance of the symptoms, a slowing down of the progression of the disease, stopping development of the disease or a disappearance of the disease. This term also includes both preventive and therapeutic treatment.

The term "therapeutically effective amount" as used here refers to a sufficient amount to have an inhibitory effect on viral replication and/or production.

The examples which follow are presented for purposes of illustration and are non-limiting.

EXAMPLES

Materials and Methods

Cell Line and Viral Strains

The experiments were carried out with Hela-P4 cells, which permit replication of the HIV-1 of subtype B used in these experiments and whose complete genome is cloned into the plasmid pNL4-3 (GenBank accession number: AF324493.1). The cells were cultivated in DMEM medium with 5% of fetal calf serum.

The plasmid pNL4-3 contains the complete genome of the wild-type strain of the HIV-1 virus. The viral strains containing mutations of resistance to antiretrovirals were obtained by directed mutagenesis by modifying the plasmid pNL4-3. The viruses used in these experiments therefore do not have other mutations. Viruses comprising the mutation E92Q (cag), E92Q (caa), G140S (age), G140S (agt), G140A (gca), Y143C (tgc) or Y143R (cgc) in the gene coding for integrase were thus obtained. These mutations correspond to the mutations most often observed in patients for whom therapy has failed. One and the same resistance mutation can be encoded by different nucleotide sequences.

Interfering RNAs

The interfering RNAs used during these experiments are double-stranded RNAs whose sequence corresponds to an miRNA included in the following list: hsa-miR-18a (SEQ ID No:2), hsa-miR-92a-1 (SEQ ID No:3), hsa-miR-185* (SEQ ID No:4), hsa-miR-219-1-3p (SEQ ID No:5), hsa-miR-370 (SEQ ID No:6), hsa-miR-518c* (SEQ ID No:7), hsa-miR-595 (SEQ ID No:8), hsa-miR-613 (SEQ ID No:9), hsa-miR-939 (SEQ ID No:10), hsa-miR-1228* (SEQ ID No:11), hsa-miR-1231 (SEQ ID No:12) and hsa-miR-1909 (SEQ ID No:13).

Transfection of the Cells 24 hours before transfection, $4 \cdot 10^4$ cells were cultured in each well of 24-well plates. The next day, the Hela-P4 cells were co-transfected with 0, 5, 10, 20 and 50 pmol of an miRNA and with 100 ng of a plasmid coding for the complete genome of a wild-type (pNL4-3) or mutated HIV-1.

This transfection was carried out by means of the Lipofectamine 2000 kit (Invitrogen). A transfection solution comprising 100 ng of pNL4-3 or of mutated pNL4-3, 5 to 50 pmol of an miRNA and 14 of Lipofectamine-2000 was diluted in 50 µL of OptiMEM medium. The Hela-P4 cells were brought into contact with this transfection solution before being incubated at 37° C. (in 5% $CO_2$) for 4 to 6 hours. The cells were then washed and put back in culture in DMEM medium with 5% of fetal calf serum.

Determination of $IC_{50}$

After transfection, the cell cultures were monitored for 6 days in order to detect the production of HIV in the supernatant by measuring the production of antigen p24 measured by ELISA (ELISA assays performed on 150 µL of cell culture supernatant) and expressed in pg/ml. In order to evaluate the capacity of the miRNA under investigation for inhibiting viral production, the p24 antigenaemia was measured in the transfected cultures with and without miRNA. The inhibitory concentration 50, i.e. the concentration of miRNA giving a decrease in the production of antigen p24 by 50%, was thus calculated.

Effects of the miRNAs on Replication of HIV-1 Resistant to Integrase Inhibitors

By measuring the production of antigen p24 at each concentration of miRNA, it was possible to define $IC_{50}$ of the different miRNAs tested. The values of these $IC_{50}$ are presented in the following table.

| Characteristics of the viral strains tested | miRNA | $CI_{50}$ pmol/mL |
|---|---|---|
| Mutation E92Q(cag) | hsa-miR-1231 | 3 |
| | hsa-miR-370 | 7 |
| | hsa-miR-18a | 11.6 |
| Mutation E92Q(caa) | hsa-miR-518c* | 4.2 |
| | hsa-miR-18a | 12 |
| | hsa-miR-595 | 6.1 |
| Mutation G140S(agc) | hsa-miR-939 | 4.3 |
| Mutation G140S(agt) | hsa-miR-939 | 7 |
| | hsa-miR-185* | 6 |
| Mutation G140A(gca) | hsa-miR-92a-1 | 11 |
| | hsa-miR-219-1-3p | 15 |
| Mutation Y143C(tgc) | hsa-miR-1909 | 2 |
| Mutation Y143R(cgc) | hsa-miR-613 | 13 |
| | hsa-miR-1228* | 9 |

These results demonstrate that the miRNAs that hybridize preferentially to the mRNAs of the gene coding for an integrase containing a mutation endowing the virus with resistance to antiretrovirals are capable of inhibiting the viral production of said strain with high efficacy.

BIBLIOGRAPHY

Ausubel et al., 1995, Current Protocols in Molecular Biology, Greene Publishing and Wiley-Interscience.

Barton and Medzhitov, Proc Natl Acad Sci USA. 2002 Nov. 12; 99(23):14943-5

Carmona et al., Mol. Pharm. 2009 Jan. 21

Chen et al., Cell Mol. Immunol. 2007 December; 4(6):473-7

Egholm et al., 1992, J. Am. Chem. Soc, 114, 1895-1897.

Maniatis et al., 1982, Molecular cloning, A laboratory Manual, Cold Spring Harbor.

Sambrook et al., 1989, Molecular cloning, A laboratory Manual, Cold Spring Harbor.

Shen et al., FEBS Lett. 2003 Mar. 27; 539(1-3):111-4

Tiscornia et al., Proc Natl Acad Sci USA. 2004 May 11; 101(19):7347-51

Xia et al., Nat. Biotechnol. 2002 October; 20(10):1006-10

Zheng et al., Blood. 2009 Mar. 19; 113(12):2646-54

The invention claimed is:

1. A method for treating an infection by a strain of a human immunodeficiency virus (HIV) that is resistant to raltegravir or elvitegravir, wherein the method comprises administering to the subject in need thereof, a therapeutically effective amount of an miRNA selected from the group consisting of hsa-miR-18a (SEQ ID NO:2), hsa-miR-92a-1 (SEQ ID NO:3), hsa-miR-185* (SEQ ID NO:4), hsa-miR-219-1-3p (SEQ ID NO:5), hsa-miR-370 (SEQ ID NO:6), hsa-miR-518c* (SEQ ID NO:7), hsa-miR-595 (SEQ ID NO:8), hsa-miR-613 (SEQ ID NO:9), hsa-miR-939 (SEQ ID NO:10), hsa-miR-1228* (SEQ ID NO:11), hsa-miR-1231 (SEQ ID NO:12) and hsa-miR-1909 (SEQ ID NO:13) or combinations thereof.

2. The method according to claim 1, wherein the HIV virus is the HIV-1 virus.

3. The method according to claim 1, wherein the strain of the HIV virus expresses a mutant integrase containing one or more mutations selected from the group consisting of E92Q, G140S, G140A, Y143R and Y143C.

4. The method according to claim 1, wherein the miRNA is administered in the form of an expression vector comprising a nucleotide sequence coding for the miRNA, or for a precursor thereof.

5. The method according to claim 1, further comprising administering simultaneously or sequentially an antiretroviral compound.

6. A pharmaceutical composition comprising at least one miRNA selected from the group consisting of hsa-miR-18a (SEQ ID NO:2), hsa-miR-92a-1 (SEQ ID NO:3), hsa-miR-185* (SEQ ID NO:4), hsa-miR-219-1-3p (SEQ ID NO:5), hsa-miR-370 (SEQ ID NO:6), hsa-miR-518c* (SEQ ID NO:7), hsa-miR-595 (SEQ ID NO:8), hsa-miR-613 (SEQ ID NO:9), hsa-miR-939 (SEQ ID NO:10), hsa-miR-1228* (SEQ ID NO:11), hsa-miR-1231 (SEQ ID NO:12) and hsa-miR-1909 (SEQ ID NO:13) or combinations thereof, and/or an expression vector comprising a nucleotide sequence coding for said miRNA or for a precursor thereof, one or more antiretroviral compounds and one or more pharmaceutically acceptable excipients and/or vehicles.

7. The composition according to claim 6, wherein said one or more antiretroviral compound is an integrase inhibitor.

8. The composition according to claim 7, wherein said integrase inhibitor is raltegravir or elvitegravir.

9. A method for treating an infection in a human by a strain of a human immunodeficiency virus (HIV) that is resistant to raltegravir or elvitegravir, wherein the method comprises administering to the human a composition comprising a therapeutically effective amount of an miRNA selected from the group consisting of hsa-miR-18a (SEQ ID NO:2), hsa-miR-92a-1 (SEQ ID NO:3), hsa-miR-185* (SEQ ID NO:4), hsa-miR-219-1-3p (SEQ ID NO:5), hsa-miR-370 (SEQ ID NO:6), hsa-miR-518c* (SEQ ID NO:7), hsa-miR-595 (SEQ ID NO:8), hsa-miR-613 (SEQ ID NO:9), hsa-miR-939 (SEQ ID NO:10), hsa-miR-1228* (SEQ ID NO:11), hsa-miR-1231 (SEQ ID NO:12) and hsa-miR-1909 (SEQ ID NO:13) or combinations thereof, and/or an expression vector comprising a nucleotide sequence coding for said miRNA or for a precursor thereof and one or more pharmaceutically acceptable excipients and/or vehicles, wherein miRNA inhibits the viral production of said strain.

10. The method according to claim 9, wherein the strain of the HIV virus expresses an integrase protein containing one or more mutated residues selected from E92Q, G140S, G140A, Y143R and Y143C.

11. The method according to claim 1, wherein the therapeutically effective amount of the miRNA is administered via the oral, sublingual, parenteral, topical, rectal or transdermal route.

12. The method according to claim 11, wherein the miRNA is administered via the oral route in the form of a tablet, a capsule, or an oral solution.

13. The method according to claim 11, wherein the miRNA administered via the parenteral route is intravenously, intradermally or subcutaneously administered and the miRNA is in the form of an injectable solution.

14. The method according to claim 9, wherein the therapeutically effective amount of the miRNA is administered via the oral, sublingual, parenteral, topical, rectal or transdermal route.

15. The method according to claim 14, wherein the miRNA is administered via the oral route in the form of a tablet, a capsule, or an oral solution.

16. The method according to claim 14, wherein the miRNA administered via the parenteral route is intravenously, intradermally or subcutaneously administered and the miRNA is in the form of an injectable solution.

* * * * *

UNITED STATES PATENT AND TRADEMARK OFFICE
CERTIFICATE OF CORRECTION

| | | |
|---|---|---|
| PATENT NO. | : 9,127,279 B2 | Page 1 of 1 |
| APPLICATION NO. | : 13/378754 | |
| DATED | : September 8, 2015 | |
| INVENTOR(S) | : Vincent Calvez and Anne-Genevieve Marcelin | |

It is certified that error appears in the above-identified patent and that said Letters Patent is hereby corrected as shown below:

In the specification

<u>Column 11,</u>
Line 27, "and 14 of" should read --and 1 µL of--.

Signed and Sealed this
Second Day of August, 2016

Michelle K. Lee
*Director of the United States Patent and Trademark Office*